United States Patent [19]

Kohno et al.

[11] Patent Number: 4,556,473
[45] Date of Patent: Dec. 3, 1985

[54] FLOW THROUGH TYPE GLASS ELECTRODE

[75] Inventors: Takeshi Kohno; Seiji Usui, both of Kyoto, Japan

[73] Assignee: Horiba, Ltd., Kyoto, Japan

[21] Appl. No.: 699,836

[22] Filed: Feb. 8, 1985

[30] Foreign Application Priority Data

Jun. 2, 1984 [JP] Japan ............................. 59-82065[U]

[51] Int. Cl.$^4$ ............................................. G01N 27/36
[52] U.S. Cl. ................................... 204/409; 204/420
[58] Field of Search ............... 204/420, 409, 411, 412, 204/1 H

[56] References Cited

U.S. PATENT DOCUMENTS

| | | | |
|---|---|---|---|
| 3,357,910 | 12/1967 | Shiller | 204/420 X |
| 3,424,664 | 1/1969 | Severinghaus | 204/420 |
| 3,840,438 | 10/1974 | Ast et al. | 204/420 X |
| 3,853,732 | 12/1974 | Brand et al. | 204/420 X |
| 4,519,890 | 5/1985 | Uematsu et al. | 204/409 |

FOREIGN PATENT DOCUMENTS

| | | | |
|---|---|---|---|
| 3010461 | 10/1981 | Fed. Rep. of Germany | 204/420 |
| 3010470 | 10/1981 | Fed. Rep. of Germany | 204/420 |

*Primary Examiner*—G. L. Kaplan
*Attorney, Agent, or Firm*—Wenderoth, Lind & Ponack

[57] ABSTRACT

A flow through type glass electrode has a resin body having a hollow interior and having bores in the opposite ends thereof extending from the outside into the interior and aligned with each other, an internal electrode positioned in the interior, a straight unitary hollow glass capillary tube extending through the bores and interior and having a uniform diameter sample flow passage therethrough, sealing members in sealing engagement around the tube and in sealing engagement in the bores where the bores open into the interior, plugs closely fitted around the tube and closely fitted in the bores where the bores open out of the body and being spaced from the sealing members along the bores to define an insulating material receiving space therebetween and extending along each bore, an insulating material filling the insulating material receiving space, and an internal liquid filling the interior.

7 Claims, 5 Drawing Figures

FLOW THROUGH TYPE GLASS ELECTRODE

BACKGROUND OF THE INVENTION

1. Field of the Invention

This invention relates to a flow through type glass electrode.

2. Description of the Prior Art

There has been proposed, as disclosed in U.S. patent application Ser. No. 614,225, filed May 24, 1984, and now U.S. Pat. No. 4,519,890, a flow-through type glass electrode which is small-sized, has superior shock resistance, can measure a minute sample, and is easy to assemble as compared with a conventional flow through type glass electrode.

This flow through type glass electrode, as shown in FIG. 4, has support tubes 23 heat-sealed to the ends of the response glass tube 22, and a sleeve 24 is heat-sealed to the support tubes 23. An internal electrode 25 and internal liquid 26 are sealed into the sleeve 24, thereby forming the main body D of the flow through type glass electrode. The main body D is contained in a resin block 27. Sample gas flows through tubes 28 equal in diameter to the response glass tube 22 and which extend through the block walls 29 respectively, the flow through tubes 28 and support tubes 23 being joined by couplers 30. Insulating material fills the main body D.

Such construction, has dead spaces 32 at the heat-sealed portions between tubes 22 and 23, and the dead space 32 and tube joint portions 33 between tubes 23 and 28 are liable to stain, which can cause clogging in the fluid passage.

Further, because of the heat-sealing, the glass of the response glass tube 22 and support tube 23 should have the same thermal expansion coefficient. Nevertheless, the flow through tube is weak in resistance to thermal shock because of low strength at the heat-sealed portions.

There is thus room for improvement in the glass electrode structure.

SUMMARY OF THE INVENTION

An object of the invention is to provide a flow through type glass electrode which is convenient to use and overcomes the above-described problems in a simple way.

This object is achieved by a flow through type glass electrode according to the invention comprising: a resin body having a hollow interior and having bores in the opposite ends thereof extending from the outside of said body into said interior and aligned with each other; an internal electrode positioned in said interior; a straight unitary hollow glass capillary tube extending through said bores and said interior and having a uniform diameter sample flow passage therethrough; sealing members in sealing engagement around said tube and in sealing engagement in said bores where said bores open into said interior; plugs closely fitted around said tube and closely fitted in said bores where said bores open out of said body and being spaced from said sealing members along said bores to define an insulating material receiving space therebetween and extending along each bore; an insulating material filling said insulating material receiving spaces; and an internal liquid filling said interior.

This flow through type glass electrode having the internal liquid filled space in the resin block through which the capillary extends has no conventional heat-sealed portions and has a strong construction which is resistant to thermal shock.

Since the glass capillary is straight and has a uniform inner diameter, and no joint portions and no heatsealed portions, useless samples are not necessary and hardly any stain remains, whereby clogging is not likely to occur.

Moreover, the single straight capillary formed of glass is easy to insert through the resin block, so that the flow through type glass electrode according to the invention can be made with considerably fewer man-hours than the prior art electrode, resulting in a considerably reduced manufacturing cost.

The above and further objects and novel features of the invention will more fully appear from the following detailed description when the same is read in connection with the accompanying drawings.

DESCRIPTION OF THE PREFERRED EMBODIMENT

Figure 1:
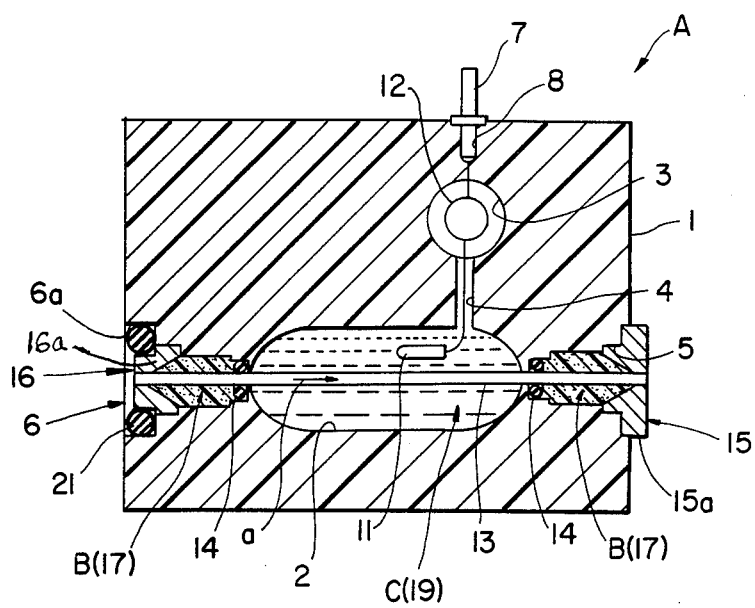
FIG. 1 is a cross-sectional plan view of an embodiment of a flow through type glass electrode according to the invention.
Figure 2:
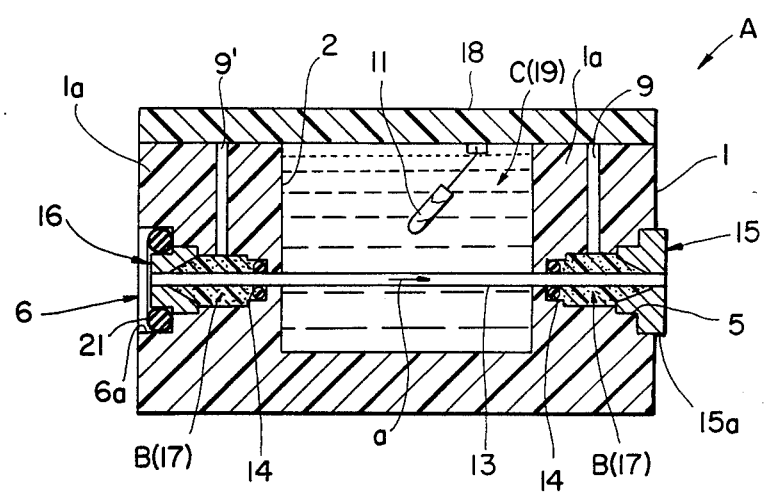
FIG. 2 is a longitudinally sectional elevation view of the embodiment of FIG. 1.
Figure 3:
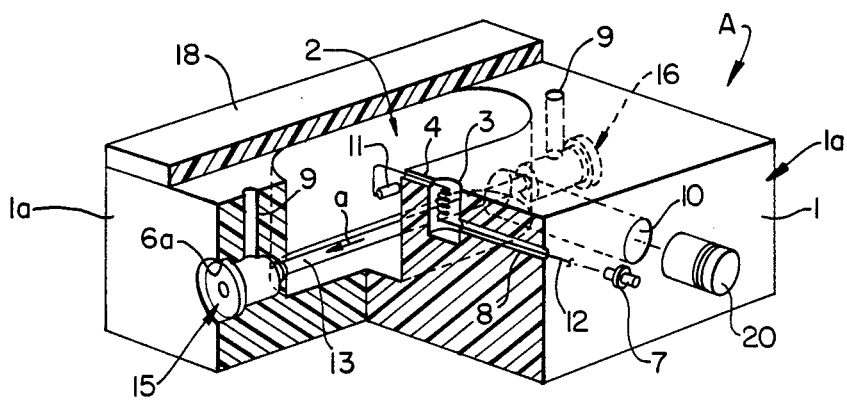
FIG. 3 is a perspective view, partly broken away, of the electrode of FIGS. 1 and 2.
Figure 4:
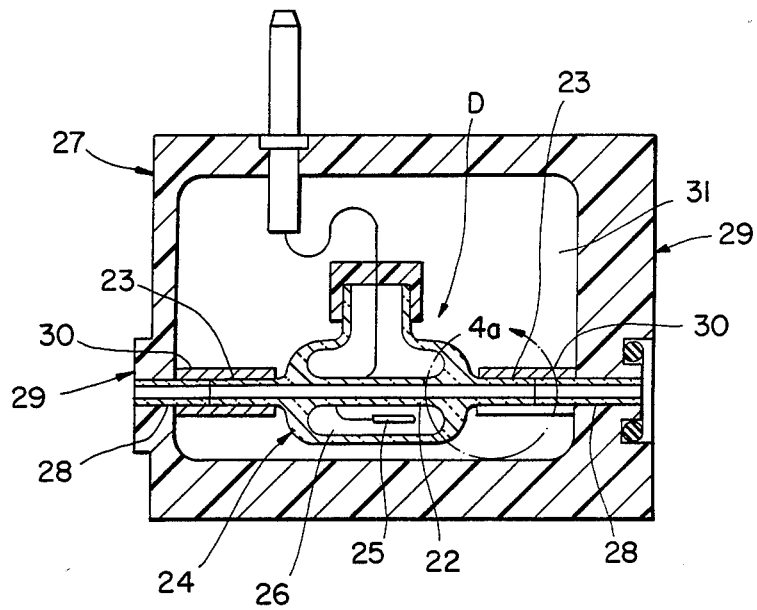
FIG. 4 is a cross-sectional plan view of a flow through type glass electrode previously proposed.
Figure 4A:
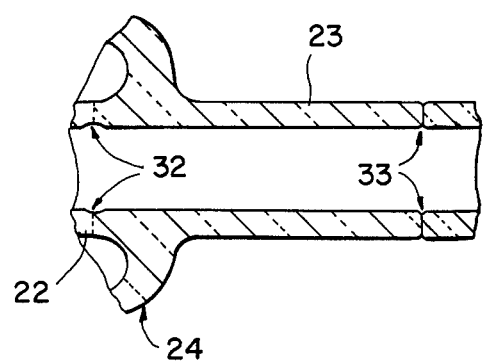
FIG. 4a is a section of the apparatus of FIG. 4.

The electrode A of the invention comprises a resin body 1 which has an elliptic cross-section, a hollow interior 2, a round bore 3 extending parallel to the axis of the interior 2, and a groove 4 extending between the recess 2 and bore 3. Through bores 5 and 6 extend outwardly from interior 2 through the end wall portions 1a at both ends of body 1 in the direction of the major diameter of the interior 2, the bores 5 and 6 being coaxial with each other and communicating with the interior 2. The bores each having a small diameter inner end, a medium diameter intermediate portion and a large diameter outer end.

A bore 8 for a connector pin 7 extends laterally into the body toward the bore 3, and filling bores 9 and 10 extend downwardly from the top of the resin body into bores 5 and 6.

An internal electrode 11 is positioned in the interior 2, and a lead wire 12 connected at one end thereof to the connector pin 7 extends from the connector pin into bore 3, is coiled in the bore 3, and then extends through the groove 4 into the interior 2 and is connected at the other end to the internal electrode 11. An insulating material (not shown) fills the space around the lead wire 11 in the groove 4.

A straight unitary, i.e. non-jointed, hollow glass capillary response tube 13 is provided which has a sample flow passage therethrough having a uniform inner diameter, and the tube 13 is inserted through the bores 5 and 6 and the interior 2 with an intermediate portion being exposed to the interior of the hollow interior 2, and has one end projecting slightly outwardly from the bore 5 in the resin body 1 and has the other end inwardly spaced from the end of the body within the bore 6 by the same amount.

Sealing members 14, such as O-rings, are provided in sealing engagement around capillary tube 13 and in the small diameter ends of bores 5 and 6 in sealing engagement with the wall portions 1a therearound.

Plugs 15 and 16 are closely fitted into the large diameter portions of bores 5 and 6 in the wall portions 1a and around the outer peripheries at both axial end portions of capillary tube 13 in the bores 5 and 6 flush with the axial end faces of the tube 13. The outer end of plug 16 is spaced inwardly of the outer end of the outer end of bore 6 to leave a large diameter portion 16a in the outer end of bore 6. A sealing ring 21 is provided around the plug 16 and projects slightly outwardly of the outer end of the plug. A portion 15a of plug 15 projects from the resin body 1 and is shaped for being closely fitted into a large diameter portion 6a of the outer end of a bore 6 in a next adjacent electrode. Thus, a plurality of flow through type glass electrodes A can be connected together in series with a plug 15 from one electrode projecting into the bore in the next electrode and seated against seal 21.

Each sealing member 14 and the corresponding plug 15 or 16 define an insulating material receiving space B which is filled with an insulating material 17, such as silicone resin, through filling bores 9.

A lid 18 of resin is positioned on the top of resin body 1 for closing interior 2 and filling bores 9. After the lid 18 closes the interior 2 to define an internal liquid space C, an internal liquid 19 is supplied into the space C through the filling bore 10, and a plug 20 is placed in the end of bore 10 to close it.

While an embodiment of the invention has been shown and described, the invention is not limited to the specific construction thereof, which is merely exemplary in the specification rather than defined.

What is claimed is:

1. A flow through type glass electrode comprising:
    a resin body having a hollow interior and having bores in the opposite ends thereof extending from the outside of said body into said interior and aligned with each other;
    an internal electrode positioned in said interior;
    a straight unitary hollow glass capillary tube extending through said bores and said interior and having a uniform diameter sample flow passage therethrough;
    sealing members in sealing engagement around said tube and in sealing engagement in said bores where said bores open into said interior;
    plugs closely fitted around said tube and closely fitted in said bores where said bores open out of said body and being spaced from said sealing members along said bores to define an insulating material receiving space therebetween and extending along each bore;
    an insulating material filling said insulating material receiving spaces; and
    an internal liquid filling said interior.

2. A flow through type glass electrode as claimed in claim 1 in which said body comprises a resin block having a recess therein opening out of one surface thereof, and a resin lid on said block closing said recess to define said interior.

3. A flow through type glass electrode as claimed in claim 2 in which the surface out of which said recess opens is substantially perpendicular to the opposite surfaces of said body out of which said bores open, and said block has bores extending from said firstmentioned surface into said insulating material receiving spaces through which insulating material can be supplied to fill said spaces and which are closed by said lid.

4. A flow through type glass electrode as claimed in claim 2 in which said block has an internal liquid filling bore extending therethrough from the outside of the block into said recess for supplying internal liquid into said recess after said lid has been placed on said block, and a plug means for plugging said internal liquid filling bore.

5. A flow through type glass electrode as claimed in claim 2 in which said block has a groove in said one surface thereof extending from said recess toward the outside of said block, and a bore means extending from said groove to the outside of said block, said internal electrode having a lead wire extending therefrom through said bore and said groove means, and a connector pin on the end of said lead wire and closing said bore means.

6. A flow through type glass electrode as claimed in claim 1 in which said plug in one of said bores is recessed inwardly from the outside of said body, and said plug in the other of said bores projects out of said body a distance the same as said one plug is recessed, whereby said electrodes can be coupled in series with the projecting plugs inserted into the one bores against said recessed plugs.

7. A flow through type glass electrode as claimed in claim 6 further comprising a seal around the end of said plug in said one bore for being engaged by a projecting plug in an adjacent electrode when the electrodes are coupled.

* * * * *